United States Patent [19]

Williams

[11] Patent Number: 4,729,781
[45] Date of Patent: Mar. 8, 1988

[54] 3,6-DICHLORO-2-METHOXYBENZOHY-DROXAMIC ACID DERIVATIVES AND USE AS HERBICIDAL AGENTS

[75] Inventor: John W. Williams, Lake Bluff, Ill.

[73] Assignee: Sandoz Ltd., Basel, Switzerland

[21] Appl. No.: 892,987

[22] Filed: Aug. 4, 1986

[51] Int. Cl.$^4$ .................... A01N 43/00; A01N 37/00; A01N 37/44; C07C 101/30

[52] U.S. Cl. .................... 71/88; 71/100; 71/111; 558/254; 560/39; 562/444; 549/438; 549/262

[58] Field of Search .................... 558/254; 560/39; 562/444; 549/438, 262; 71/100, 111, 88

[56] References Cited

U.S. PATENT DOCUMENTS

| 3,013,054 | 12/1961 | Richter | 558/254 |
| 3,702,863 | 11/1972 | Neighbors | 558/254 |
| 4,161,488 | 7/1979 | Plattner et al. | 558/254 |

FOREIGN PATENT DOCUMENTS 0133155 6/1983 European Pat. Off. ............ 558/254

Primary Examiner—Henry R. Jiles
Assistant Examiner—Robert C. Whittenbaugh
Attorney, Agent, or Firm—Gerald D. Sharkin; Richard E. Vila

[57] ABSTRACT

Disclosed are herbicidal compounds of the general formula I:

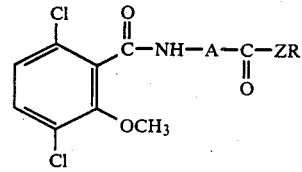

wherein A is O-alkylene of 1 to 5 carbon atoms, O-alkenylene of 3 to 6 carbon atoms in which the unsaturation is non-adjacent the oxygen atom thereof or NH-alkylene in which the alkylene is of 1 to 5 carbon atoms, and —COZR is an acid function or forms certain ester or thioester functions, and the mono- and di-salt forms thereof.

36 Claims, No Drawings

3,6-DICHLORO-2-METHOXYBENZOHYDROXAMIC ACID DERIVATIVES AND USE AS HERBICIDAL AGENTS

The present invention relates to compounds which are derivatives of 3,6-dichloro-2-methoxybenzoic acids, particularly benzohydroxamic acid derivatives, their use as herbicides and to agricultural compositions containing the same.

The present invention more particularly relates to compounds of the formula I:

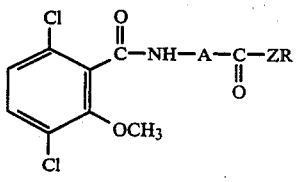

wherein

A is O-alkylene of 1 to 5 carbon atoms, O-alkenylene of 3 to 6 carbon atoms in which the unsaturation is non-adjacent the oxygen atom thereof or NH-alkylene in which the alkylene is of 1 to 5 carbon atoms, the O- and NH- thereof being attached to the NH which is adjacent to A, Z is oxygen or sulfur, R is H, $C_1$-$C_{12}$alkyl, $C_3$-$C_8$alkenyl, $C_3$-$C_8$alkynyl, $C_2$-$C_{10}$haloalkyl containing 1 to 6 halogens of atomic weight of 18 to 80, $C_2$-$C_{10}$alkoxyalkyl, cycloalkyl or cycloalkenyl of 3 to 8 ring carbon atoms optionally substituted by 1 or 2 halogens of atom weight of 18 to 80 or $C_1$-$C_2$alkyl groups, cycloalkylalkyl or cycloalkenylalkyl of 4 to 10 carbon atoms in the alkyl portion is of 1 to 3 carbon atoms and the cycloalkyl or cycloalkenyl ring is of 3 to 8 carbon atoms and is optionally mono- or di-ring substituted by halo of atom weight of 18 to 80 or $C_1$-$C_2$alkyl groups or

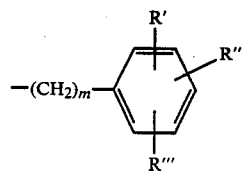

m is 0 to 3,

R' and R" are independently H, $C_1$-$C_4$alkyl, $C_1$-$C_4$alkoxy, $C_1$-$C_4$alkylthio, $CF_3$, halo of atomic weight of from 18 to 80 or $NO_2$, R''' is H, $C_1$-$C_3$alkyl or halo of atomic weight of 18 to 80, or two of R', R" and R''' together form $C_1$-$C_2$alkylenedioxy with the other being H, and the salt forms thereof.

When in the compounds of the formula I, A is O-alkylene or NH-alkylene, the alkylene may be straight chain or branched. Any such branching, e.g. methyl groups, may occur once or twice on any carbon atom of the linear portion of the alkylene moiety. Preferably, the alkylene portion of the O-alkylene moiety is of 1 to 3 carbons and contains no more than a single methyl branch, or is unbranched. More preferably, A is —OCHR$_1$—, wherein R$_1$ is H or methyl, and it is particularly preferred that A is o-methylene, i.e —OCH$_2$—.

When A is O-alkenylene, the alkenylene portion may also be straight chain or branched. Preferably, the connecting linear alkenylene portion is of 3 or 4 carbon atoms and contains no more than a single methyl branch or is unbranched, and is more preferably unbranched, eg. allylene.

In general, Z is preferably oxygen.

When R is or contains an alkyl, alkenyl, alkynyl or alkoxy group, the same may be straight chain or branched, provided that any alkenyl or alkynyl group desirably comprises at least a three linear carbon atom chain. When R is alkyl, it is preferably $C_1$-$C_8$alkyl, branched or unbranched, more preferably $C_1$-$C_6$alkyl. When R is haloalkyl, it preferably contains one or two halogen atoms or one or two $CF_3$ groups. When R is or contains a cycloalkyl or cycloalkenyl group, such group is preferably unsubstituted. When R is cycloalkylalkyl or cycloalkenylalkyl, the alkyl portion may be straight chain or branched, but is more preferably unbranched and of 1 or 2 carbon atoms, and it particularly preferred that such alkyl is methyl (—CH$_2$—). When R is or contains phenyl, it is generally preferred that m is 0 or 1. Preferably, the phenyl portion or group is unsubstituted, mono-substituted or disubstituted. In particular, it is generally preferred that R' is H, $C_1$-$C_4$alkyl, $C_1$-$C_2$alkoxy, $CF_3$, halo of atomic weight of from 18 to 80 or nitro, R" is H and R''' is H, $C_1$-$C_2$alkyl or halo of atomic weight of from 18 to 80. More preferably, R' is H, $C_1$-$C_3$alkyl, methoxy, $CF_3$, F, Cl or nitro, R" is H and R''' is H, $CH_3$, F or Cl.

The alkali metal and ammonium salts are the generally preferred salt forms. When R is H and disalt forms may be produced, the mono-salt forms are generally preferred.

The compounds of the formula I in which A is O-alkylene or O-alkenylene in free base form may be prepared in a Procedure A by reacting the compound of the formula II:

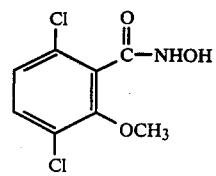

with a compound of the formula III:

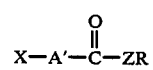

wherein Z and R are as above defined, A' is alkylene of 1 to 5 carbon atoms or alkenylene of 3 to 6 carbon atoms in which the unsaturation is non-adjacent X and X is halo, preferably chloro or bromo.

Procedure A may be carried out at temperatures of from about 25° C. to 150° C., preferably 60° C. to 120° C. in the presence of a base and in a solvent media. Preferred bases are the alkali metal hydroxides such as sodium hydroxide or potassium hydroxide. Preferred solvents are the lower alkanols such as methanol or ethanol or a mixture of water and a lower alkanol, e.g. water and ethanol. The desired product of the formula I may be isolated and recovered by working up by established procedures.

The compounds of the formula I in which A is NH-alkylene in free base form may be prepared in a Procedure B by reacting the compound of the formula IV:

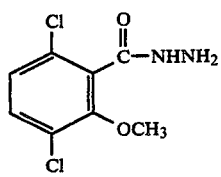

with a compound of the formula V:

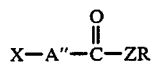

wherein Z and R are as above defined, X is halo, preferably chloro or bromo, and A″ is alkylene of 1 to 5 carbon atoms.

Procedure B may be carried out at temperatures of from about 20° C. to 120° C., preferably 40° C. to 90° C., in the presence of a base and in a solvent media. A typically preferred base for such reaction is sodium carbonate. Preferred solvents include the acyclic and cyclic ethers such as tetrahydrofuran. The desired product may be isolated and recovered from the Procedure B reaction mixture by working up by standard procedures.

The compounds of the formula I in which R is other than H may be produced from other compounds of the formula I in which R is other than H by the well-known process of transesterification (Procedure C). In such procedure a compound of the formula I is subjected to reaction with the alcohol or thioalcohol corresponding to the ester desired to be formed, i.e. a compound HZR (Compound VI) in the presence of transesterification catalyst and in a liquid media of conventional type. Transesterification catalysts are well known and include the Lewis acids such as the metal alkoxides, e.g. titanium n-butoxide. Such procedure is generally carried out in a known manner to shift the equilibrium of reaction system in favor of the desired ester of the formula I such as by causing removal in predetermined form from the reaction solvent media of the —ZR moiety of the starting material desired to be replaced, e.g. by forming the corresponding alcohol HOR which is selectively evaporated from the reaction media. The reaction may be carried out at varying temperatures typically of from about 25° C. to 150° C., more typically about 50° C. to 120° C., and in a conventional solvents which are typically chosen as appropriate in accordance with the predetermined plan for the reaction. The preferred starting compounds of the formula I are those in which —ZR is O—$C_1$-$C_2$alkyl, more preferably the methyl ester, and the equilibrium shifted in favor of the desired ester of the formula I by evaporating the resulting $C_1$-$C_2$alkanol. For example, the methanol from the preferred methyl ester starting material may be evaporated from an inert aromatic solvent such as toluene. The resulting desired ester of the formula I may be isolated and recovered from the Procedure C reaction by working up by established procedures.

The compounds of the formula I have the tautomeric form:

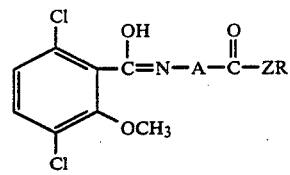

wherein A, Z and R are as defined. Such enols of the compounds I are of acid character and form, and accordingly the compounds I will also form salts even when R is other than H. Since the compounds in which R is H form salts, the compounds of the formula I in which R is H form di-salts. When R is H, salt formation preferentially takes at the ZH site, such that the mono-salt forms of those in which such R is H are those in which such R is the salt-forming cation at such location.

The mono- and di-salts forms of the compounds of the formula I may be prepared in a conventional manner by reacting a compound of the formula I with a salt forming base in a solvent media. Temperatures may vary widely but are usually in the range of 0° C. to 100° C., more typically 10° C. to 60° C. Solvents typically employed for such salt formation include the ethers and mixtures thereof with water. When the mono-salt form of the compounds I in which R is H is desired, the formation of such mono-salt in good yield by avoiding substantial quantities of the di-salt form may be effected by various established techniques such as control of the amount of salt-forming base employed or by taking advantage of the differential solubility of the desired mono-salt form in the reaction solution. Also, the mono-salt forms may be prepared by using an excess of the salt-forming reagent to thereby form to di-salt and subjecting the di-salt to moderate heating under high vacuum to form the mono-salt from the di-salt form. Heating at temperatures of from 60° C. to 120° C. for 12 to 36 hours is usually adequate to form the mono-salts from the di-salts. In general, the salt forms of the compounds I may be isolated and recovered by employing standard procedures.

The compounds of the formula I generally form salts with bases and all such salt forms are included within the invention. In addition to exhibiting herbicidally activity of similar character to the parent non-salt forms, the various salt forms may also be employed to prepare other salt forms by employing well-known procedures. While the preparation of the salt forms has been separately described above, such preparation may take place in conjunction with or prior to recovery in other type procedures hereinabove described for preparation of the compounds of the formula I, in which case the desired salt may be recovered or converted to the salt free form by employing standard procedures.

The preferred salt forms of the compounds of the formula I are the alkali metal salts, particularly the sodium and potassium salts, and the ammonium salt forms including the secondary and tertiary ammonium salt forms. Merely representative of some of the wide variety of secondary and tertiary ammonium salt forms are the dimethylammonium salt, isopropylammonium salt, diethanolammonium salt, triethanolammonium salt and the 2-hydroxyethyloxyethylammonium salt. Other salt forms which may be prepared include the hydrazinium salt forms which may be derived from unsubstituted or substituted hydrazine, e.g. hydrazine, $NH_2N(CH_2CH_3)_2$ and the like.

The compound of the formula II employed in Procedure A may be prepared from 3,6-dichloro-2-methoxybenzoic acid chloride as described in Step B of Example 1 hereinafter. The compound of the formula IV employed in Procedure B may be also prepared from 3,6-dichloro-2-methoxybenzoic acid chloride as described in Step B of Example 6 hereinafter. The preparation of 3,6-dichloro-2-methoxybenzoic acid chloride is described in Step A of Example 1 hereinafter. The various other starting materials used in preparation of the compounds of the formula I and its salts are either known or may be prepared from known materials by conventional methods.

The compounds of the formula I (including the salts thereof) are useful because they control the growth of plants. By plants it is meant germinating seeds, emerging seedlings and established vegetation including underground portions. In particular, the compounds are useful as herbicides as indicated by causing damage to both monocotyledoneous and dicotyledoneous plants in various standard evaluations for determining such effects. The herbicidal effects are exhibited both pre- and post-emergence the plants. Such herbicidal effects indicate that the compounds of the formula I are particularly of interest in combatting weeds (unwanted plants) in a locus in which such weeds are present.

The compounds of the formula I are indicated mainly to be stronger acting against dicotyledeneous plants than monocotyledoneous plants. Relatively less toxicity towards crops than towards weeds is further indicated. Hence, the compounds are of particular interest as selective herbicides to combat weeds in a crop locus, particularly a locus of a monocotyledoneous crop such as, for example, corn (maize), oats, rice, wheat, sorghum and the like, especially corn.

The present invention therefore also provides a method of combatting weeds in a locus which comprises applying to the locus a herbicidally effective amount of a compound of the invention. When selective action is desired in a crop locus, the amount applied will be sufficient to combat weeds without substantially damaging the crop.

For general herbicidal as well as selective herbicidal use of the compounds of the invention, the particular amounts to be applied will vary depending upon recognized factors such as the compound employed, the plants primarily in the locus, the timing, mode and formulation in application, the various conditions of treatment such as soil and weather and the like. However, in general, satisfactory results in weed control are usually obtained upon application of the compounds of the invention at a rate in the range of from 0.1 to 10 Kg./hectare, more usually 0.3 to 5 Kg./hectare, and preferably 0.5 to 3 Kg./hectare, the application being repeated as necessary. When used in crops, the application usually will not exceed about 5 Kg./hectare, and is usually in the range of 0.1 to 4 Kg./hectare, preferably 0.5 to 3 Kg./hectare.

For practical use as herbicides, the compounds of the formula I may be and are preferably employed in herbicidal compositions comprising a herbicidal effective amount of the compound and an inert carrier which is agriculturally acceptable in the sense of not, by reason of its presence, poisoning the agricultural environment including the immediate soil of application or any crops present therein or otherwise being unsafe for application. Such compositions or formulations may contain 0.01% to 99% by weight of active ingredient, from 0 to 20% by weight of agriculturally acceptable surfactants and 1 to 99.9% by weight of the inert carrier. Higher ratios of surfactant to active ingredient are sometimes desirable and are achieved by incorporation into the formulation or by tank mixing. Application forms of composition typically contain between 0.01 and 25% by weight of active ingredient, but lower or higher levels of active ingredient can, of course, be present depending on the intended use and the physical properties of the compound. Concentrate forms of composition intended to be diluted before use generally contain between 2 and 90%, preferably between 10 and 80% by weight of active ingredient.

Useful compositions or formulations of the compounds of the invention include dusts, granules, pellets, suspension concentrates, wettable powders, emulsifiable concentrates and the like. They are obtained by conventional manner, e.g. by mixing the compounds of the invention with the inert carrier. More specifically, liquid compositions are obtained by mixing the ingredients, fine solid compositions by blending and, usually grinding, suspensions by wet milling and granules and pellets by impregnating or coating (preformed) granular carriers with the active ingredient or by agglomeration techniques.

For example, dusts can be prepared by grinding and blending the active compound with a solid inert carrier such as the talcs, clays, silicas, pyrophyllite and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

Alternatively, the compounds of the invention may be used in microencapsulated form.

Agriculturally acceptable additives may be employed in the herbicidal compositions to improve the performance of the active ingredient and to reduce foaming, caking and corrosion.

Surfactant as used herein means agriculturally acceptable material which imparts emulsifiability, spreading, wetting, dispersibility or other surface-modifying properties. Examples of surfactants are sodium lignin sulphonate and lauryl sulphate.

Carriers as used herein mean a liquid or solid material used to dilute a concentrated material to a usable or desirable strength. For dusts or granules it can be e.g. talc, kaolin or diatomaceous earth, for liquid concentrate forms, a hydrocarbon such as xylene or an alcohol such as isopropanol; and for liquid application forms, e.g. water or diesel oil.

The compositions of this invention can also comprise other compounds having biological activity, e.g. compounds having similar or complementary herbicidal activity or compounds having antidotal, fungicidal or insecticidal activity.

A typical herbicidal composition, according to this invention, is illustrated by the following Examples A and B in which the quantities are in parts by weight.

EXAMPLE A

Preparation of a Dust

Product of Example 2: 10

Powdered Talc: 90

The above ingredients are mixed in a mechanical grinder-blender and are ground until a homogeneous, free-flowing dust of the desired particle size is obtained. This dust is suitable for direct application to the site of the weed infestation.

EXAMPLE B

Preparation of Wettable Powder

25 Parts of a compound of formula I, e.g. the compound of Example 2 hereinafter, are mixed and milled with 25 parts of synthetic fine silica, 2 parts of sodium lauryl sulphate, 3 parts of sodium ligninsulphonate and 45 parts of finely divided kaolin until the mean particle size is about 5 micron. The resulting wettable powder is diluted with water before use to a spray liquor with the desired concentration.

EXAMPLE C

Preparation of Emulsifiable Concentrate (EC)

13.37 parts of the compound of Example 7 are mixed in a beaker with 1.43 parts of Toximul 360A (a mixture of anionic and non-ionic surfactants containing largely anionic surfactants), 5.61 parts of Toximul 360A (a mixture of anionic and non-ionic surfactants containing largely non-ionic surfactants), 23.79 parts of dimethylformamide and 55.8 parts of Tenneco 500-100 (predominantly a mixture of alkylated aromatics such as xylene and ethylbenzene) until solution is effected. The resulting EC is diluted with water for use.

EXAMPLE 1

[(3,6-Dichloro-2-methoxybenzoyl)aminooxy]acetic acid

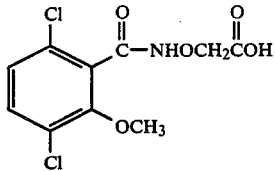

Step A: 3,6-Dichloro-2-methoxybenzoyl chloride

To 4.0 kg thionyl chloride, was added 5.0 kg of 3,6-dichloro-2-methoxybenzoic acid. This was stirred and heated to reflux (ca. 60° C.) for 1.5 hours. The reaction mixture was allowed to cool and excess thionyl chloride evaporated in vacuo. The crude product was then distilled under reduced pressure to give 3,6-dichloro-2-methoxybenzoyl chloride as a liquid, b.p. 117° C. @ 0.6 mm Hg.

Step B: 3,6-Dichloro-2-methoxybenzohydroxamic acid

To a solution of 360 g. of potassium carbonate in 350 ml. of water was added 2.5 diethyl ether and 181 g. hydroxylamine hydrochloride. The mixture was cooled to 5°–10° C. and 477 g. of 3,6-dichloro-2-methoxybenzoyl chloride was added dropwise at a rate that maintained the reaction temperature below 10° C. After addition was complete, the reaction mixture was stirred for 1 hour and allowed to stand overnight at ambient temperature. The crude white solid product was obtained by filtration. The crude solid was washed with water, then treated with 1.5 of 4.5 M. HCl, filtered, washed again with H$_2$O and dried to give 3,6-dichloro-2-methoxybenzohydroxamic acid as a white solid, m.p. 150° C.

Step C: [(3,6-Dichloro-2-methoxybenzoyl)aminooxy]acetic acid

To a solution of 86.34 g. of sodium hydroxide in 1.2 W of water was added 900 ml. of 95% ethanol and 240 g. of 3,6-dichloro-2-methoxybenzohydroxamic acid. To aid dissolution, an additional 300 ml. 95% ethanol and 60 ml. H$_2$O were added. A solution of 153.12 g. bromoacetic acid in 120 ml. of 95% ethanol was then added to the reaction mixture over 0.5 hours, followed by 60 ml. of water. The mixture was then heated to reflux for 3 hours, cooled to ambient temperature, and 150 ml. 20% HCl added. The reaction mixture was then extracted twice with ethyl acetate. The ethyl acetate solutions were combined, washed with brine, and dried over MgSO$_4$ overnight, then filtered and solvent evaporated in vacuo. The residue was crystallized from chloroform to yield [(3,6dichloro-2methoxybenzoyl)aminooxy]acetic acid as a white solid in two crops (m.p. 145°–154° C.).

EXAMPLE 2

Methyl [(3,6-dichloro-2-methoxybenzoyl)aminooxy]acetate

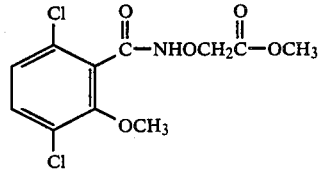

To a solution of 2.15 g. of potassium hydroxide in 50 ml. of methanol was added 7.55 g. of 3,6-dichloro-2-methoxy benzohydroxamic acid followed by stirring until dissolution was obtained. To this solution was added dropwise 3.03 ml. methylbromoacetate in 25 ml. of methanol. The reaction mixture was refluxed for 2 hours and allowed to stir overnight at ambient temperature. To the reaction mixture was added 0.36 g. of additional potassium hydroxide and the mixture heated to reflux for 4 hours, then cooled, filtered, and the filtrate concentrated in vacuo to give a crude semi-solid product. This crude product was taken up in methylene chloride and washed with water, 5% aqueous NaHCO$_3$, brine, then dried over MgSO$_4$, filtered and evaporated in vacuo to give a viscuous oil. The oil crystallized from an ethyl acetate-hexane mixture to the title product as a white solid, m.p. 102°–105° C.

EXAMPLE 3 n-Butyl[(3,6-dichloro-2-methoxybenzoyl)aminooxy]acetate

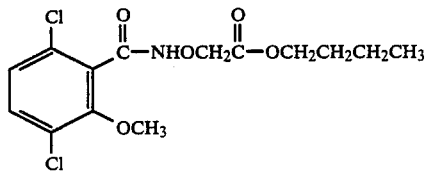

To 161.8 g. of methyl[(3,6-dichloro-2-methoxybenzoyl) aminooxy]acetate was added 80 g. of n-butyl alcohol, 600 ml. of toluene, and 9.5 g. of titanium n-butoxide. The mixture was stirred and heated to 85° C. for 2 hours to drive off a methanol/toluene mixture. The heat was then maintained at 95°-100° C. to distill off n-butanol/toluene. The reaction mixture was cooled to 40° C. and 150 ml. of 1 M. HCl added. The mixture was then washed with 1 M. HCl, water, then saturated NaHCO₃ solution, and then dried over MgOS₄, filtered, and evaporated in vacuo to yield the title product as a white solid, m.p. 68°-71° C.

EXAMPLE 4

Dimethylammonium[(3,6-dichloro-2-methoxy)-benzoyl) aminooxy]acetate

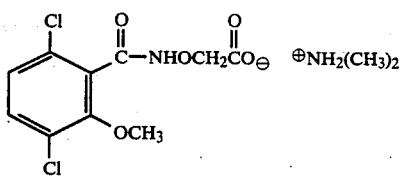

To a solution of excess dimethylamine in diethyl ether (prepared by shaking 50 ml. of 40% aqueous dimethylamine and 50 ml. of diethyl ether and decanting the ether layer) was added a solution of 3 g. of [(3,6-dichloro-2-methoxybenzoyl) aminooxy]acetic acid in 50 ml. of tetrahydrofuran. During the addition, an oil formed and settled out. After 1 hour, the ether/THF layer was decanted and the resulting oil was washed several times with ethyl acetate and dried under high vacuum at 100° C. for 24 hours to obtain the titled salt as a foamy solid which hardens on standing.

EXAMPLE 4A

The following additional mono-salts may be readily prepared.

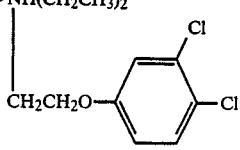

| Ex. No. | R | Character |
| --- | --- | --- |
| 4A-1 | Na⊕ | M.P. 150-160° C. (dec.) |
| 4A-2 | ⊕NH₂(CH₂CH₃)₂ | light brown glass |
| 4A-3 | ⊕NH₃CH(CH₃)₂ | tan foamy solid |
| 4A-4 | ⊕NH₃(CH₂)₂O(CH₂)₂OH | amber oil |
| 4A-5 | ⊕NH(CH₂CH₃)₂ \ CH₂CH₂OC—(CH₂)₄CH₃ ‖ O | amber oil |
| 4A-6 | ⊕NH(CH₂CH₃)₂ \ CH₂CH₂O—[Cl,Cl-phenyl] | yellow glass |

EXAMPLE 5

[(3,6-Dichloro-2-methoxybenzoyl)aminooxy]acetic acid bis-isopropylamine salt

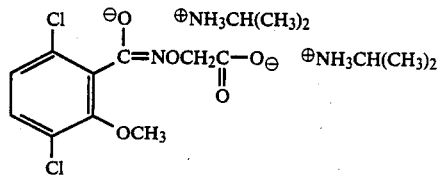

To a solution of 4.0 g. of [3,6-dichloro-2-methoxybenzoyl)aminooxy]acetic acid in 250 ml. diethyl ether was added 1.6 ml. of isopropylamine. The resulting mixture was stirred for 15 minutes and the resulting solid collected by vacuum filtration. The crude solid was washed with three portions of diethyl ether and dried under high vacuum at ambient temperature to obtain the titled di-salt form as a foamy tan solid.

EXAMPLE 5A

Following the basic procedure of Example 5 there was also obtained the [(3,6-dichloro-2-methoxybenzoyl)aminooxy]acetic acid bis-diethylamine salt as light brown glass.

EXAMPLE 6

Ethyl[(3,6-dichloro-2-methoxybenzoyl)hydrazino]acetate

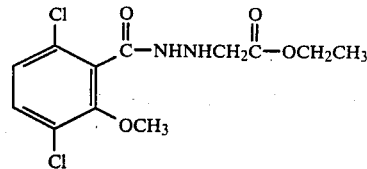

Step A: 3,6-Dichloro-2-methoxybenzoylhydrazine

To a solution of 0.22 mol. hydrazine in 100 ml. chloroform at −10° C. was added 0.1 mol. of 3,6-dichloro-2-methoxybenzoyl chloride. The mixture was stirred at ambient temperature for 2 hours, filtered, and the filtrate evaporated in vacuo. The residue was crystallized from methanol and water, then recrystallized from chloroform and hexane to obtain the titled product, m.p. 144°-145° C.

Step B: Ethyl[(3,6-dichloro-2-methoxybenzoyl)hydrazine]acetate

To a solution of 8 g. of 3,6-dichloro-2-methoxybenzoyl hydrazine and 7 g. of ethyl bromoacetate in 200 ml. of tetrahydrofuran, was added 8 g. sodium carbonate. The resulting mixture was stirred at ambient temperature for 16 hours, then refluxed for 8 hours and filtered. The filtrate was evaporated in vacuo to yield a crude solid which was recrystallized from diethyl ether to obtain the titled product as a white crystalline solid, m.p. 93°-96° C.

Additional representative compounds of the invention are exemplified below with reference to the structural formula I.

| Ex. No. | A | R | m.p. (°C.) |
| --- | --- | --- | --- |
| 7 | —OCH₂— | O—isopropyl | 88-92 |

-continued

| Ex. No. | A | R | m.p. (°C.) |
|---|---|---|---|
| 8 | " | O—ethyl | 57-61 |
| 9 | " | S—methyl | — |
| 10 | " | O—n-propyl | 44-47 |
| 11 | " | O—t-butyl | 141-143 |
| 12 | " | O—isobutyl | 68-68.5 |
| 13 | " | O—sec-butyl | 111-112 |
| 14 | " | O—sec-pentyl | 70-72 |
| 15 | " | O—hexyl | 63-64.5 |
| 16 | —O—CH$_2$—<br>\|<br>CH$_3$ | O—methyl | 102.5-103 |
| 17 | " | O—ethyl | thick oil |
| 18 | —CH$_2$CH$_2$CH$_2$— | O—methyl | yellow semi-solid |
| 19 | —OCH$_2$— | O—cyclopentyl | 82-85 |
| 20 | " | O—CH$_2$CF$_3$ | 79-82 |
| 21 | " | O—CH—CF$_3$<br>\|<br>CF$_3$ | 159-161 |
| 22 | " | O—p-chlorophenyl | 139-140 |
| 23 | " | O—benzyl | 130-131 |
| 24 | —OCH$_2$CH=CH— | O—ethyl | 78-82 |
| 25 | " | O—methyl | oily solid |
| 26 | —OCH$_2$CH$_2$CH$_2$ | H | thick oil |
| 27 | —NHCH—<br>\|<br>CH$_3$ | O—ethyl | yellow liquid |
| 28 | —OCH$_2$— | O—pentyl | 64-65° C. |
| 29 | " | O—octyl | waxy solid |
| 30 | " | O—decyl | colorless oil |
| 31 | " | O—CH$_2$CH=C(CH$_3$)$_2$ | 57-58 |
| 32 | " | O—cyclopropylmethyl | 45-50 |
| 33 | " | O—phenyl | — |
| 34 | " | O—m-methylbenzyl | 106-107 |
| 35 | " | O—o-methylbenzyl | 102-104 |
| 36 | " | O—p-methylbenzyl | 155-157 |
| 37 | " | O—p-isopropylbenzyl | 141-143 |
| 38 | " | O—o-chlorobenzyl | 97-98 |
| 39 | " | O—m-chlorobenzyl | 103-105 |
| 40 | " | O—2,6-dichlorobenzyl | 161-162 |
| 41 | " | O—2,4-dichlorobenzyl | 107-108 |
| 42 | " | O—3,4-dichlorobenzyl | 120-121 |
| 43 | " | O—o-fluorobenzyl | 67-70 |
| 44 | " | O—3,5-dichlorobenzyl | 95-97 |
| 45 | " | O—m-fluorobenzyl | 95-97 |
| 46 | " | O—p-fluorobenzyl | 133-134 |
| 47 | " | O—m-CF$_3$—benzyl | 94-95 |
| 48 | " | O—p-CF$_3$—benzyl | 140-141 |
| 49 | " | O—o-methoxybenzyl | 75-78 |
| 50 | " | O—m-methoxybenzyl | 65-70 |
| 51 | " | O—p-methoxybenzyl | 145-146 |
| 52 | " | O—3,4-methylenedioxybenzyl | 117-118 |
| 53 | " | O—o-nitrobenzyl | 105-106 |
| 54 | " | O—p-nitrobenzyl | 128-129 |
| 55 | " | O—3-methyl-4-nitrobenzyl | 97-98 |
| 56 | " | O—3-nitro-4-chlorobenzyl | 134-135 |
| 57 | " | S—benzyl | 118-119 |

Compound of Example 4A-2

The compound of Example 4A-2, above, was prepared as follows: To a solution of 4.0 g. of 3,6-dichloro-2-methoxy-benzoylaminooxyacetic acid in 300 ml. of diethyl/ether was added dropwise with stirring 1.16 ml. of isopropylamine. A gummy solid formed and after 15 minutes of stirring, the ether was evaporated in vacuo. The residue was dissolved in methanol and then evaporated in vacuo to yield a solid foam. After drying under high vacuum at ambient temperature, the tan solid foam analyzed correctly by 'H NMR as the desired 1-methylethylammonium 3,6-dichloro-2-methoxybenzoylaminooxyacetate.

The herbicidal toxicity of the compounds of this invention can be illustrated by established testing techniques known to the art, such as pre- and post-emergence testing.

The herbicidal activity of the compounds of this invention was demonstrated by experiments carried out for the pre-emergence control of a variety of weeds. In these experiments small plastic greenhouse pots filled with dry soil were seeded with the various weed seeds. Twenty-four hours or less after the seeding, the pots were sprayed with water until the soil was wet and the test compounds formulated as aqueous emulsions of acetone solutions containing emulsifiers were sprayed at the indicated concentrations on the surface of the soil.

After spraying, the soil containers were placed in the greenhouse and provided with supplementary heat as required and daily or more frequent watering. The plants were maintained under these conditions for a period of from 14 to 21 days, at which time the condition of the plants and the degree of injury to the plants was rated on a scale of from 0 to 10, as follows: 0=no injury, 1, 2 =slight injury, 3, 4=moderate injury, 5, 6=moderately severe injury, 7, 8, 9=severe injury, 10=death and NE indicated not emerged. The pre-emergence herbicidal activity of representative compounds is demonstrated by the following data set out in Tables 1, 3, 4 and 5.

The herbicidal activity of the compounds of this invention was also demonstrated by experiments carried out for the post-emergence control of a variety of weeds. In these experiments the compounds to be tested were formulated as aqueous emulsions and sprayed at the indicated dosage on the foliage of the various weed species that have attained a prescribed size. After spraying, the plants were placed in a greenhouse and watered daily or more frequently. Water was not applied to the foliage of the treated plants. The severity of the injury was determined 21 days after treatment and was rated on the scale of from 0 to 10 heretobefore described. The effectiveness of representative compounds as post emergence herbicides is demonstrated by the data set forth below in Tables 2 and 6.

TABLE 1

Pre-emergence Herbicidal Activity
Compounds of Examples 1 and 3

| | Rates of Application (lbs./acre) | | | | | | | |
|---|---|---|---|---|---|---|---|---|
| | Compound of Example 1 | | | | Compound of Example 3 | | | |
| | 0.25 | 0.125 | 0.062 | 0.031 | 0.25 | 0.125 | 0.062 | 0.031 |
| Wild Mustard | 10 | 9 | 9 | 7 | 9 | 10 | 7 | 6 |
| Bindweed | 10 | 9 | 7 | 2 | 9 | 9 | 6 | 3 |
| Pigweed | 10 | 9 | 5 | 1 | 9 | 9 | 5 | 0 |
| Jimsonweed | 10 | 9 | NE | 1 | NE | NE | 3 | NE |
| Velvet Leaf | 10 | 10 | 9 | 1 | 9 | 5 | 4 | 5 |
| Morningglory | 10 | 10 | 9 | 7 | 9 | 9 | 7 | 5 |
| Yellow Foxtail | 3 | 0 | 0 | 0 | 6 | 0 | 0 | 0 |
| Barnyard Grass | 7 | 1 | 1 | 0 | 8 | 3 | 0 | 0 |
| Johnson | NE | 1 | 0 | 0 | 8 | 6 | 0 | 0 |

TABLE 1-continued

Pre-emergence Herbicidal Activity
Compounds of Examples 1 and 3

| | Compound of Example 1 | | | | Compound of Example 3 | | | |
|---|---|---|---|---|---|---|---|---|
| | Rates of Application (lbs./acre) | | | | | | | |
| | 0.25 | 0.125 | 0.062 | 0.031 | 0.25 | 0.125 | 0.062 | 0.031 |
| Grass Wild Oats | 3 | 1 | 0 | 0 | 2 | 1 | 0 | 0 |
| Crabgrass | 0 | 0 | 0 | 0 | 7 | 0 | 0 | 0 |
| Sprangletop | 0 | 0 | 0 | 0 | 1 | 0 | 0 | 0 |
| Cheatgrass | 7 | 0 | 0 | 0 | 3 | 4 | 0 | 0 |
| Soybeans | 10 | 10 | 9 | 8 | 9 | 10 | 8 | 7 |
| Cotton | 9 | 7 | 5 | 2 | 9 | 8 | 5 | 5 |
| Pintobean | 10 | 10 | 9 | 9 | 9 | 9 | 8 | 8 |
| Alfalfa | 10 | 7 | 0 | 0 | 9 | 9 | 5 | 3 |
| Wheat | 7 | 4 | 1 | 0 | 6 | 5 | 4 | 1 |
| Rice | 9 | 6 | 1 | 0 | 9 | 6 | 5 | 0 |
| Sorghum | 6 | 2 | 0 | 0 | 9 | 6 | 5 | 0 |
| Corn | 0 | 0 | 0 | 0 | 1 | 0 | 0 | 0 |
| Oats | 2 | 0 | 0 | 0 | 2 | 1 | 1 | 0 |
| Yellow Nutsedge | NE | 0 | 0 | 0 | 9 | 0 | 8 | 0 |

TABLE 2

Post-emergence Herbicidal Activity
Compounds of Examples 1 and 3

| | Compound of Example 1 | | | | Compound of Example 3 | | | |
|---|---|---|---|---|---|---|---|---|
| | Rates of Application (lbs./acre) | | | | | | | |
| Plant | 0.25 | 0.125 | 0.062 | 0.031 | 0.25 | 0.125 | 0.062 | 0.031 |
| Wild Mustard | 9 | 10 | 9 | 8 | 9 | 7 | 8 | 5 |
| Bindweed | 10 | 10 | 8 | 4 | 8 | 7 | 5 | 3 |
| Pigweed | 9 | 10 | 10 | 7 | 10 | 10 | 10 | 3 |
| Jimsonweed | 10 | 10 | 9 | 4 | 9 | 9 | 9 | 9 |
| Velvet Leaf | 10 | 8 | 3 | 4 | 9 | 7 | 5 | 3 |
| Morningglory | 10 | 10 | 7 | 6 | 9 | 9 | 9 | 9 |
| Yellow Foxtail | 5 | 0 | 0 | 0 | 6 | 2 | 0 | 0 |
| Barnyard Grass | 1 | 0 | 0 | 0 | 8 | 6 | 1 | 0 |
| Johnson Grass | 7 | 2 | 0 | 0 | 3 | 2 | 0 | 0 |
| Wild Oats | 0 | 0 | 0 | 0 | 0 | 0 | 0 | 0 |
| Crabgrass | 0 | 0 | 0 | 0 | 0 | 0 | 0 | 0 |
| Sprangletop | 0 | 0 | 0 | 0 | 0 | 0 | 0 | 0 |
| Cheatgrass | 0 | 0 | 0 | 0 | 0 | 0 | 0 | 0 |
| Soybeans | 10 | 10 | 9 | 8 | 9 | 9 | 7 | 8 |
| Cotton | 9 | 8 | 7 | 4 | 5 | 5 | 4 | 4 |
| Pintobean | 10 | 10 | 10 | 9 | 10 | 9 | 9 | 9 |
| Alfalfa | 9 | 8 | 4 | 2 | 7 | 5 | 1 | 0 |
| Wheat | 3 | 1 | 0 | 0 | 2 | 1 | 0 | 0 |
| Rice | 1 | 0 | 0 | 0 | 0 | 0 | 0 | 0 |
| Sorghum | 0 | 0 | 0 | 0 | 1 | 0 | 0 | 0 |
| Corn | 0 | 0 | 0 | 0 | 3 | 0 | 0 | 0 |
| Oats | 0 | 0 | 0 | 0 | 0 | 0 | 0 | 0 |
| Yellow Nutsedge | 0 | 0 | 0 | 0 | 0 | 0 | 0 | 0 |

TABLE 3

Pre-emergence Herbicidal Activity
Compounds of Examples 2, 4, 5 and 6

| | Example 4 | | Example 5 | | Example 6 | | Example 2 | |
|---|---|---|---|---|---|---|---|---|
| | Rate of Application (lbs./acre) | | | | | | | |
| Plant | 0.25 | .125 | 0.25 | .125 | 0.25 | .125 | 0.25 | .125 |
| Velvetleaf | 9 | 7 | 9 | 7 | 8 | 6 | 10 | 10 |
| Pigweed | 9 | 9 | 9 | 9 | 8 | 6 | 10 | 9 |
| Wild Mustard | 9 | 9 | 9 | 7 | 7 | 6 | 10 | 9 |
| Bindweed | 9 | 7 | 10 | 5 | 7 | 6 | 10 | 10 |
| Jimsonweed | NE | 6 | NE | 8 | 8 | 6 | 10 | 9 |
| Morningglory | 9 | 9 | 9 | 9 | 7 | 6 | 10 | 10 |
| Cotton | 9 | 7 | 8 | 7 | 8 | 6 | 10 | 9 |
| Soybeans | 9 | 9 | 9 | 9 | 10 | 9 | 10 | 9 |
| Sorghum | 5 | 2 | 6 | 3 | 0 | 0 | 7 | 5 |
| Wild Oats | 2 | 1 | 3 | 1 | 0 | 0 | 3 | 1 |
| Cheatgrass | 3 | 0 | 4 | 2 | 0 | 0 | 9 | 3 |
| Yellow Nutsedge | NE | 0 | 2 | 2 | 0 | 0 | 1 | 0 |
| Crabgrass | 3 | 0 | NE | 5 | 0 | 0 | 9 | 0 |
| Barnyard Grass | 3 | 1 | 8 | 4 | 0 | 0 | 9 | 8 |
| Yellow Foxtail | 2 | 0 | 5 | 3 | 0 | 0 | 3 | 0 |
| Johnson Grass | 7 | 2 | 8 | 1 | 0 | 0 | 7 | 6 |
| Sprangletop | 4 | 0 | 1 | 0 | 0 | 0 | 0 | 0 |
| Alfalfa | 9 | 8 | 9 | 9 | 8 | 8 | 10 | 9 |
| Rice | 8 | 6 | 6 | 3 | 2 | 0 | 9 | 9 |
| Corn | 0 | 0 | 0 | 0 | 0 | 0 | 0 | 0 |
| Oats | 1 | 0 | 2 | 0 | 0 | 0 | 1 | 1 |
| Wheat | 5 | 4 | 6 | 4 | 2 | 0 | 7 | 5 |
| Pintobean | 10 | 9 | 10 | 9 | 9 | 8 | 10 | 10 |

TABLE 4

Pre-emergence Herbicidal Activity
Compounds of Examples 19, 20, 23 and 24

| | Example 19 | | Example 20 | | Example 23 | | Example 24 | |
|---|---|---|---|---|---|---|---|---|
| | Rate of Application (lbs./acre) | | | | | | | |
| Plant | 0.25 | .125 | 0.25 | .125 | 0.25 | .125 | .125 | .125 |
| Velvetleaf | 9 | 7 | 10 | 10 | 9 | 7 | 9 | 8 |
| Pigweed | 9 | 7 | 9 | 10 | NE | 10 | 9 | 8 |
| Wild Mustard | 9 | 8 | 10 | 9 | NE | NE | 9 | NE |
| Bindweed | 9 | 9 | 10 | 9 | 9 | 9 | 6 | 4 |
| Jimsonweed | 8 | NE | 10 | 8 | NE | NE | NE | 7 |
| Morningglory | 9 | 10 | 10 | 10 | 9 | 8 | 9 | 9 |
| Cotton | 7 | 9 | 9 | 8 | 9 | 6 | 8 | 7 |
| Soybeans | 10 | 10 | 10 | 9 | 10 | 9 | 9 | 9 |
| Sorghum | 7 | 3 | — | — | 4 | 0 | — | — |
| Wild Oats | 1 | 1 | 3 | 0 | 0 | 0 | 3 | 0 |
| Cheatgrass | 4 | 4 | 4 | 1 | 4 | 1 | 3 | 1 |
| Yellow Nutsedge | NE | NE | 0 | 0 | NE | 4 | NE | 0 |
| Crabgrass | 2 | 3 | 0 | 0 | 5 | 0 | 2 | 5 |
| Barnyard Grass | 7 | 4 | 9 | 2 | 4 | 5 | 1 | 0 |
| Yellow Foxtail | 5 | 0 | 4 | 0 | 8 | 3 | 0 | 0 |
| Johnson Grass | 7 | 6 | 7 | 7 | 8 | 1 | 0 | 5 |
| Sprangletop | 2 | 1 | — | — | 7 | 1 | — | — |
| Alfalfa | 9 | 9 | — | — | 9 | 9 | — | — |
| Rice | 6 | 5 | — | — | 8 | 7 | — | — |
| Corn | 0 | 0 | 1 | 0 | 2 | 0 | 0 | 0 |
| Oats | 1 | 0 | — | — | 0 | 0 | — | — |
| Wheat | 6 | 4 | 5 | 3 | 6 | 4 | 2 | 1 |
| Pintobean | 10 | 10 | — | — | 9 | 9 | — | — |

TABLE 5

Pre-emergence Herbicidal Activity
Compounds of Examples 7 and 15

| | Compound of Example 7 | | | Compound of Example 15 | | |
|---|---|---|---|---|---|---|
| | Rates of Application (lbs./acre) | | | | | |
| Plant | 0.25 | 0.125 | 0.062 | 0.25 | 0.125 | 0.062 |
| Wild Mustard | 10 | 9 | 9 | 9 | 9 | 7 |
| Bindweed | 9 | 9 | 4 | 9 | 9 | 8 |
| Pigweed | 9 | 7 | 4 | 9 | 6 | 5 |
| Jimsonweed | NE | 7 | 6 | NE | NE | 9 |
| Velvet Leaf | 10 | 9 | 4 | 9 | 9 | 5 |
| Morningglory | 10 | 9 | 8 | 9 | 10 | 7 |

TABLE 5-continued

Pre-emergence Herbicidal Activity
Compounds of Examples 7 and 15

| | Rates of Application (lbs./acre) | | | | | |
|---|---|---|---|---|---|---|
| | Compound of Example 7 | | | Compound of Example 15 | | |
| Plant | 0.25 | 0.125 | 0.062 | 0.25 | 0.125 | 0.062 |
| Yellow Foxtail | 1 | 0 | 0 | 5 | 1 | 0 |
| Barnyard Grass | 8 | 5 | 1 | 8 | 7 | 4 |
| Johnson Grass | 2 | 3 | 0 | 8 | 5 | 0 |
| Wild Oats | 2 | 1 | 0 | 1 | 1 | 0 |
| Crabgrass | 9 | 0 | 0 | 8 | 0 | 0 |
| Sprangletop | 0 | 0 | 0 | 5 | 0 | 0 |
| Cheatgrass | 7 | 1 | 0 | 3 | 2 | 0 |
| Soybeans | 10 | 10 | 9 | 10 | 9 | 7 |
| Cotton | 9 | 8 | 6 | 9 | 6 | 5 |
| Pintobean | 10 | 9 | 9 | 10 | 9 | 7 |
| Alfalfa | 10 | 4 | 0 | 9 | 8 | 4 |
| Wheat | 5 | 2 | 1 | 4 | 4 | 3 |
| Rice | 9 | 9 | 0 | 9 | 9 | 4 |
| Sorghum | 6 | 2 | 0 | 4 | 1 | 0 |
| Corn | 0 | 0 | 0 | 3 | 0 | 0 |
| Oats | 1 | 0 | 0 | 1 | 1 | 0 |
| Yellow Nutsedge | 1 | 0 | 0 | 3 | 3 | 0 |

TABLE 6

Post-emergence Herbicidal Activity
Compounds of Examples 7 and 15

| | Rates of Application (lbs./acre) | | | | | |
|---|---|---|---|---|---|---|
| | Compound of Example 7 | | | Compound of Example 15 | | |
| Plant | 0.25 | 0.125 | 0.062 | 0.25 | 0.125 | 0.062 |
| Wild Mustard | 9 | 9 | 9 | 9 | 9 | 9 |
| Bindweed | 10 | 10 | 8 | 5 | 3 | 5 |
| Pigweed | 10 | 10 | 9 | 10 | 10 | 10 |
| Jimsonweed | 10 | 10 | 8 | 9 | 9 | 9 |
| Velvet Leaf | 9 | 8 | 6 | 8 | 7 | 6 |
| Morningglory | 10 | 10 | 9 | 9 | 9 | 9 |
| Yellow Foxtail | 4 | 2 | 0 | 4 | 0 | 0 |
| Barnyard Grass | 4 | 1 | 0 | 6 | 4 | 1 |
| Johnson Grass | 8 | 2 | 0 | 3 | 2 | 0 |
| Wild Oats | 3 | 1 | 0 | 0 | 0 | 0 |
| Crabgrass | 0 | 0 | 0 | 0 | 0 | 0 |
| Sprangletop | 0 | 0 | 0 | 0 | 0 | 0 |
| Cheatgrass | 0 | 0 | 0 | 0 | 0 | 0 |
| Soybeans | 10 | 10 | 9 | 8 | 8 | 7 |
| Cotton | 9 | 8 | 5 | 5 | 4 | 6 |
| Pintobean | 10 | 10 | 10 | 10 | 10 | 9 |
| Alfalfa | 9 | 9 | 7 | 3 | 0 | 0 |
| Wheat | 7 | 3 | 1 | 2 | 1 | 0 |
| Rice | 1 | 0 | 0 | 0 | 0 | 0 |
| Sorghum | 0 | 0 | 0 | 0 | 0 | 0 |
| Corn | 0 | 0 | 0 | 3 | 0 | 0 |
| Oats | 3 | 1 | 0 | 0 | 0 | 0 |
| Yellow Nutsedge | 0 | 0 | 0 | 0 | 0 | 0 |

What is claimed is:

1. A compound of the formula:

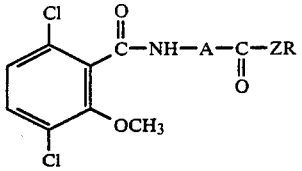

wherein
A is O-alkylene of 1 to 5 carbon atoms, O-alkenylene of 3 to 6 carbon atoms in which the unsaturation is non-adjacent the oxygen atom thereof or NH-alkylene in which the alkylene is 1 to 5 carbon atoms, the O— and NH— thereof being attached to the NH which is adjacent to A, Z is oxygen or sulfur, R is H, $C_1$–$C_{12}$alkyl, $C_3$–$C_8$alkenyl, $C_3$–$C_8$alkynyl, $C_2$–$C_{10}$haloalkyl containing 1 to 6 halogens of atomic weight of 18 to 80, $C_2$–$C_{10}$alkoxyalkyl, cycloalkyl or cycloalkenyl of 3 to 8 ring carbon atoms optionally substituted by 1 or 2 halogens of atom weight of 18 to 80 or $C_1$–$C_2$alkyl groups, cycloalkylalkyl or cycloalkenylalkyl of 4 to 10 carbon atoms in the alkyl portion is of 1 to 3 carbon atoms and the cycloalkyl or cycloalkenyl ring is of 3 to 8 carbon atoms and is optionally mono- or di-ring substituted by halo of atom weight of 18 to 80 or $C_1$–$C_2$alkyl groups or

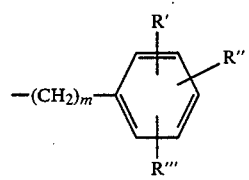

m is 0 to 3,

R' and R" are independently H, $C_1$–$C_4$alkyl, $C_1$–$C_4$alkoxy, $C_1$–$C_4$alkylthio, $CF_3$, halo of atomic weight of from 18 to 80 or $NO_2$, R" is H, $C_1$–$C_3$alkyl or halo of atomic weight of 18 to 80, or two of R', R" and R''' together form $C_1$–$C_2$alkylenedioxy with the other being H, in non-salt or in salt form.

2. A compound of claim 1 in which A is O-alkylene of 1 to 5 carbon atoms.

3. A compound of claim 2 in which A is —OCHR$_1$— wherein R$_1$ is H or methyl.

4. A compound of claim 3 in which A is —OCH$_2$—.

5. A compound of claim 4 in which Z is O and R is $C_1$–$C_{12}$alkyl.

6. A compound of claim 5 in which R is $C_1$–$C_6$alkyl in non-salt form.

7. The compound of claim 6 in which R is methyl.

8. The compound of claim 6 in which R is ethyl.

9. The compound of claim 6 in which R is hexyl.

10. The compound of claim 6 in which R is isopropyl.

11. The compound of claim 6 in which R is n-butyl.

12. The compound of claim 6 in which R is t-butyl.

13. The compound of claim 4 in which Z is O and R is H in non-salt form.

14. A compound of claim 4 in which R is a salt-forming cation, in such mono-salt form.

15. A compound of claim 14 in which the salt-forming cation is an alkali metal or ammonium cation.

16. A compound of claim 1 in which Z is O.
17. A compound of claim 1 in non-salt form.
18. A compound of claim 4 in which Z is O and R is

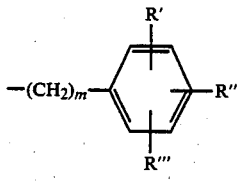

19. A compound of claim 18 in which m is 0 or 1, R' is H, $C_1$-$C_4$alkyl, $C_1$-$C_2$alkoxy, $CF_3$, halo of atomic weight of from 18 to 80 or nitro, R'' is H and R''' is H, $C_1$-$C_2$alkyl, or halo of atomic weight of from 18 to 80.
20. A compound of claim 19 in which m is 0.
21. A compound of claim 19 in which m is 1.
22. A compound of claim 16 in which A is O-alkenylene of 3 to 6 carbon atoms.
23. A compound of claim 16 in which A is NH-alkylene of 1 to 5 carbon atoms.
24. A compound of claim 23 in which A is NH—$CH_2$—.
25. A compound of claim 4 in which Z is O and R is cycloalkyl or cycloalkenyl of 3 to 8 ring carbon atoms optionally substituted by 1 or 2 halogens of atomic weight of 18 to 80 or $C_1$-$C_2$alkyl groups.
26. A compound of claim 25 in which the cycloalkyl or cyclolkenyl is unsubstituted.
27. The compound of claim 26 in which R is cyclopentyl, in non-salt form.
28. An agricultural composition comprising an inert agriculturally acceptable carrier and a herbicidally effective amount of a compound of claim 1.
29. A method of combatting weeds in a locus comprising applying to said locus a herbicidally effective amount of a compound of claim 1.
30. The method of claim 29 in which Z is O and A is —$OCH_2$—.
31. The method of claim 30 in which said locus comprises both weeds and a monocotyledoneous crop and the compound is applied at a rate herbicidally effective to the weeds and ineffective to substantially damage said crop.
32. The method of claim 31 in which R is $C_1$-$C_{12}$-alkyl.
33. The method of claim 32 in which R is $C_1$-$C_6$alkyl.
34. The method of claim 33 in which R is n-butyl and the compound is in non-salt form.
35. The method of claim 32 in which the crop is a corn crop.
36. The method of claim 35 in which the compound is applied pre-emergence the weeds and crop.

* * * * *